United States Patent [19]

Gadekar

[11] 4,052,509

[45] Oct. 4, 1977

[54] METHOD FOR REDUCING SERUM URIC ACID LEVELS

[75] Inventor: Shreekrishna M. Gadekar, Trenton, N.J.

[73] Assignee: Affiliated Medical Research, Inc., Princeton, N.J.

[21] Appl. No.: 686,650

[22] Filed: May 14, 1976

Related U.S. Application Data

[60] Division of Ser. No. 530,684, Dec. 9, 1974, Pat. No. 3,974,281, which is a continuation-in-part of Ser. No. 380,655, July 19, 1973, abandoned, which is a continuation-in-part of Ser. No. 315,836, Dec. 18, 1972, Pat. No. 3,839,346.

[51] Int. Cl.$^2$ .............................................. A61K 31/44
[52] U.S. Cl. .................................................... 424/263
[58] Field of Search .......................................... 424/263

[56] References Cited

U.S. PATENT DOCUMENTS

| | | | |
|---|---|---|---|
| 3,644,626 | 2/1972 | Witzel | 424/263 |
| 3,655,897 | 4/1972 | Witzel | 424/263 |
| 3,715,358 | 2/1973 | Witzel et al. | 424/263 |
| 3,721,676 | 3/1973 | Witzel et al. | 260/296 R |

OTHER PUBLICATIONS

The Merck Manual, of Diagnosis and Therapy, 12th Edition, (1972), pp. 1101-1107.

*Primary Examiner*—Norman A. Drezin
*Attorney, Agent, or Firm*—Dorfman, Herrell and Skillman

[57] ABSTRACT

Novel pharmaceutical compositions containing as the active ingredient the compound 5-methyl-1-phenyl-2-(1H)-pyridone are described. Such compositions have been found to have a metabolic property which causes significant lowering of serum uric acid levels in humans and other mammals. The compositions containing 5-methyl-1-phenyl-2-(1H)-pyridone caused no irritation on oral administration or when applied to specific target tissues showed no significant irritation or other sequelae.

6 Claims, No Drawings

METHOD FOR REDUCING SERUM URIC ACID LEVELS

CROSS REFERENCE TO RELATED APPLICATIONS

This application is a division of U.S. patent application Ser. No. 530,684, filed Dec. 9, 1974 now U.S. Pat. No. 3,974,281, which, in turn, was a continuation-in-part of U.S. patent application Ser. No. 380,655, filed July 19, 1973, now abandoned, which, in turn, was a continuation-in-part of patent application Ser. No. 315,836, filed Dec. 18, 1972, now issued as U.S. Pat. No. 3,839,346.

BACKGROUND OF THE INVENTION

The present invention relates to novel pharmaceutical compositions containing as the active ingredient the compound 5-methyl-1-phenyl-2-(1H)-pyridone (AMR-69) having the formula

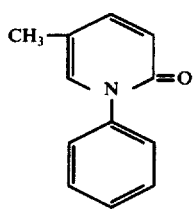

I

Certain substituted pyridones and particularly those wherein the N-substituents are phenylamine derivatives are known to possess analgesic qualities. Several of the latter are disclosed in British Pat. No. 1,238,959 and U.S. Pat. Nos. 2,947,754 and 2,947,755. None of these compounds, during the intervening years, have exhibited sufficient potency and/or safety to provide commercially acceptable therapeutic compositions.

A number of alkyl substituted pyridones have been illustrated in the Examples of U.S. Pat. Nos. 3,644,626 and 3,655,897. The examples given in these patents and the patents cited above would seem to teach that the most effective pyridones would be those having an aminophenyl N-substituent. There is no indication given that a composition having the structure of the present invention with the methyl and phenyl radicals assuming, respectively, the 5 and 1 positions, on the pyridone ring would give the enhanced therapeutic properties and concomitant low toxicity as set forth below.

Pyridones such as those described above have generally been prepared either by ring closure of the appropriate diol intermediates (U.S. Pat. No. 2,947,754) which are expensive, when available; by the reaction of cyanoacetanilide with 2,4-diketones (Chem. Abst. 72, 308); by the catalytic dehydrogenation of the appropriate dihydro-2-pyridone (J. Org. Chem. 26, 2586) or by the reaction of an appropriate 2-(1H)-pyridone alkali metal salt (which is prepared by reaction of the pyridone with an alkali metal hydride) with the appropriate halogenated aryl compound in overall yields of about 15–25% (British Pat. No. 1,238,959, page 9) (U.S. Pat. No. 2,947,755). As will be apparent to those skilled in the art, these processes are difficult, uneconomical and often result in poor yields after extended manipulation of expensive starting materials.

While 5-methyl-1-phenyl-2-(1H)-pyridone has been used as a starting material and as an intermediate in the synthesis of various pyridones reported to have therapeutic properties, there is no disclosure that this specific pyridone itself would have effective therapeutic properties in treating subjects having a wide range of symptoms.

SUMMARY OF THE INVENTION

I have discovered that 5-methyl-1-phenyl-2-(1H)-pyridone (AMR-69) has excellent analgesic activity, marked anti-inflammatory activity and shows excellent anti-pyretic activity in test animals when compared with the standard analgesic drug (aminopyrine). Further as compared to this standard, the compound of the present invention, when formulated into dosage form for oral or intraperitoneal administration, showed markedly lower toxicity in test animals. Moreover, AMR-69 has been observed to show markedly lower toxicity, as well as enhanced therapeutic activity when compared with closely related homologues such as 1-phenyl-2-(1H)-pyridone, 5-ethyl-1-phenyl-2-(1H)-pyridone or 3-methyl-1-phenyl-2-(1H)-pyridone.

Additionally, I have found that the AMR-69 causes significant lowering of uric acid levels in the serum after oral administration. This lowering of uric acid levels was without any deposition of uric acid or its salts in either the joints or other organs of the body. The exact mechanism for this uric acid clearance has not been established by no clinically deleterious sequelae were noted. The lowering of uric acid is desirable in individuals prone to episodes of gout. (Primer on the Rheumatic Diseases, 7th Edition, pages 102–103, (Arthritis Foundation)). Treatment with AMR-69 has also been observed to effect significant lowering of serum glucose levels (blood sugar) in the test animals.

Furthermore, AMR-69 has been observed to be therapeutically effective in protecting mucous membranes of the respiratory system, in particular those of the nasopharynx and lungs, against noxious agents. Protection against noxious focal respiratory tract pathology (petechiae, edema, hemorrhage, focal infection, etc.) has been demonstrated in gross examination of rat lung tissues and microscopic examination of dog lung tissues following treatment with AMR-69. Special protective effects of the mucous linings of the respiratory system have been confirmed in tests on humans, especially those showing symptoms of sinusitus, post-nasal drip, chronic rhinitis infection, allergic rhinitis, conjunctivitis, headache, earache or sore throat. The therapeutic effectiveness of AMR-69 treatment on skin conditions such as dermatitis, insect sting and poison ivy have also been demonstrated.

Administration of AMR-69 over extended periods caused no untoward side reactions. The compound is more readily soluble than other analgesic uricosuric agents, is very rapidly absorbed in the blood stream and is relatively non-irritating to the various body tissues at effective dosage levels. It may be administered orally, topically, parenterally intradermally, by inhalation spray in formulations containing conventional non-toxic pharmaceutically acceptable carriers, adjuvants and vehicles. The term parenteral as used herein includes subcutaneous injections, intravenous, intramuscular, intracisternal or intrathecal injection or infusion techniques.

Further, in the course of preparing the above compound for formulation into the therapeutic compositions of the invention, I have discovered a novel process for its synthesis, as described and claimed in my issued U.S. Pat. No. 3,839,346, starting from commercially available, comparatively inexpensive raw materials by a straighforward simple procedure which yields the desired compound in purified form in higher yields than have heretofore been available. Further, as I perfected this process, I have found that it is useful for the synthesis of an entire range of N-aromatic-substituted pyridones. These previously could only be achieved from difficult starting materials or via derivatives which required the use of extremely caustic and dangerous reactants such as the alkali metal hydrides and which even with the use of such reactants afforded the desired compounds in comparatively poor yields.

The present invention is directed to affording pharmaceutical compositions wherein 5-methyl-1-phenyl-2-(1H)-pyridone (AMR-69) is formulated, together with a pharmaceutically acceptable solid carrier, diluent or coating; a liquid carrier, solvent, or diluent or a gaseous carrier, to provide pharmaceutical compositions in forms suitable for therapeutic administration to mammalian species, especially to animals such as horses, bovines, swine, dogs, cats, rats, mice, etc., as well as to humans.

The solid carriers are useful in subdividing the material into pills, tablets, powders or cachets for immediate or sustained release or where desirable into suppositories or bougies. Solid diluents may include flavors or therapeutic adjuvants. The liquid carrier can provide flavorful vehicles for oral administration. In properly liquid form adjusted as to tonicity, the active compound may be prepared into solution or liquid suspension for injectable administration. The gaseous carriers or diluents ar useful in preparing the active ingredient for aerosol administration, where indicated In the above compositions, the active material, together with its solid diluent or carrier, can be pressed into dosage forms such as pills or tablets or encapsulated for sustained release; or it can be buffered so as to dissolve in isotonic solutions for administration by injection, It can also be dispersed in suitable semi-solid crriers or liquid for topical administration for local or systemic effect.

While AMR-69 is an effective analgesic and uricosuric agent and can be utilized by itself in therapy, it may also be combined with other therapeutic agents to obtain the combined effects of AMR-69 with such agents. The typical agents with which it may be combined are other analgesics, sedatives, diuretics, stimulants, antiarrhythmics, tranquilizers, etc. The only pharmacological incompatibility would be with CNS stimulants which may amplify pain beyond the analgesic capabilities of AMR-69. AMR-69 appears to exercise its effects by a different enzyme system than aspirin, it may advantageously be combined with aspirin in therapeutic compositions according to this invention to achieve the combined effects of these agents, neither of which generates phenylhydrazine derivatives during catabolism.

The standard pharmaceutically acceptable carriers normally used in such pharmaceutical formulations can be utilized in formulating the aforesaid compositions of this invention.

As described in my U.S. Pat. No. 3,839,346, a process is provided for the synthesis of pyridones of the formula

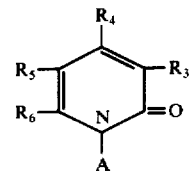

wheren A is an aromatic group; $R_3$, $R_4$, $R_5$ and $R_6$ are individually each hydrogen, alkyl, aryl or substituted aryl; which comprises the steps of reacting a pyridone of the formula

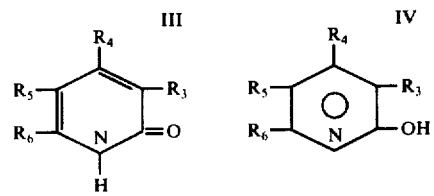

in which $R_3$, $R_4$, $R_5$ and $R_6$ are as set forth above, with a halogenated compound of the formula AX, wherein X is either chlorine, bromine or iodine, at temperatures ranging between the melting point and boiling point of said halogenated compound, in the presence of an alkali metal carbonate and finely divided metallic copper. The synthesis of AMR-69 by this process is illustrated in Example 1 of the Section on Detailed Description.

The term "aromatic group" as utilized in describing the A elements in this invention refers to aryl or aromatic groups as defined in Karrer, Paul, "Organic Chemistry", 1938, Elsevier Publishers (English edition) part II page 339; and includes the "aromatic-like heterocyclic groups" as defined in the same text and reference at pages 691-693. Among such aryl groups are phenyl, 3-nitrophenyl; 4-methoxyphenyl; p-tolyll; 3'-trifluoromethylphenyl; 4'-chlorophenyl; 2'-naphthyl; 1'-naphthyl; etc. The preferred substituent among the aryl compounds is the phenyl group. As is mentioned above, the compound containing this substituent, i.e. 5-methyl-1-phenyl-2-(1H)-pyridone (AMR-69) is the one which I have found to be most effective as an analgesic, as well as having a strikingly low level of toxicity.

Among the aromatic-like heterocyclic groups are those heterocyclic compounds listed by Karrer and described as having an aromatic nature, including 2-thienyl; 2-furyl; 5'-quinolyl, 4'-pyridyl, 3'-pyridyl, 2'-pyridyl, 2'-quinolyl, 4'-quinolyl, 2'-thiazolyl, 2'-imidazolyl.

The $R_3$, $R_4$, $R_5$ and $R_6$ radicals may individually each be hydrogen, alkyl groups having up to 6 carbon atoms, aryl or substituted aryl or even aromatic groups as defined above.

The reaction is preferably achieved in the liquid state but in the absence of solvent diluents and consequently should be performed at temperatures ranging between the melting point and the boiling point of the reactants. Since the halogenated compound having the formula AX is usually the lower melting component, its melting point fixes the lower temperature for the reaction. As the reaction proceeds, a eutectic may form from the intersolution of the reactants or of the reaction products. If desired, the temperature may be adjusted accordingly. However, in the interest of maintaining the speed of the reaction, it is preferred to operate above this minimum temperature and the reaction may be conducted at temperatures up to the boiling point of the lowest boiling component of the reaction mixture. It is preferred not to conduct the reaction in a solvent but a solvent, inert to the reactants and to the reaction products, may be utilized.

I have found that conversion of the initial pyridone having formula III to its alkali metal salt by reaction of the pyridone with the alkali metal hydride as taught by the prior art is not necessary. Instead, I avoid this conversion and conduct the reaction within the above-described temperature range in the presence of an alkali metal carbonate and finely divided metallic copper.

As the reaction proceeds without the need for the alkali metal hydrides, previous precautions concerning absolute anhydrous conditions and inert gas atmospheres are not necessary. However, it is preferred to use the alkali metal carbonate in excess of the stoichemetric amount needed to react with the halogen, in substantially anhydrous form as this provides the alkali metal carbonate in its most concentrated form. Among the useful alkali metal carbonates are potassium carbonate, cesium carbonate, sodium carbonate and lithium carbonate. Potassium carbonate is preferred.

The finely divided copper which is used for this reaction may be any copper powder in finely subdivided form. Because of the malleability of copper, grindings of copper are not fine enough and do not possess sufficient surface area to provide the preferred highly activated copper which promotes the reaction at the desired rate. The preferred form of finely divided copper to be utilized for the present reaction is the copper resulting from the precipitation of copper sulfate solutions ($CuSO_4$) by the addition thereto of zinc dust. Various techniques exist for the preparation of such highly activated coppers (cf. Organic Synthesis, Vol. 2, (1943), pg. 446).

DETAILED DESCRIPTION AND EXAMPLES
BIO-ASSAY RESULTS WITH 5-METHYL-1-PHENYL-2-(1H)-PYRIDONE (AMR-69)

Analgesic Activity

The end-point for analgesic testing in rats with the hind limb inflammed is based on the absence of a squeal in response to flexion of the inflammed ankle joint (Method described by S. Margolin, Proceedings of an International Symposium on Non-Steroidal Anti-Inflammatory Drugs, Excerpta Medica International Congress, Series No. 82, 1964). By this procedure, the oral $ED_{50}$ (median analgesic dose) for AMR-69 is 145± 26 mg./kg. The comparison standard was amino-pyrine, which has an oral $ED_{50}$ of 150± 26 mg./kg. AMR-69 by the oral route is as effective as aminopyrine as an analgesic effect with AMR-69 as compared to aminopyrine was noted during the tests.

Anti-inflammatory Activity

Anti-inflammatory activity was assayed by the method described by Margolin (ibid). utilizing albino rats. The antiinflammatory bio-assay basis is the ability to reduce the edema (swelling) when an experimental inflammation is induced in the hind limb of the rats. The oral medium effective dose ($ED_{50}$) in rats for AMR-69 is 200± 46 mg./kg. The median effective dose for amino-pyrine is 185± 31 mg./kg. Here too, a more rapid onset of the therapeutic effect was noted.

Anti-pyretic Activity

Anti-pyretic activity testing is based upon the ability of the drug to suppress the experimentally-induced fever in albino rabbits (F.M. Berger, et. al. Pharmacology and Experimental Therapeutics, Vol. 127, No. 1, 1959 based upon the original presentations of G. Brownlee Quart. J. Pharm; Vol. 10, Page 609, 1937 and Quart. J. Pharm., Vol. 12, Page 45, 1939). The drugs under test are administered intraperitoneally and the response is compared to that of saline controls. The average change in temperature over a period of three hours following the administration of aminopyrine (100 mg./kg. i.p.), AMR-69 (100 mg./kg. i.p.) and the saline (isotonic) controls were as follows:

Saline Controls: +0.9 ±0.17° C
Aminopyrine (Standard) −0.6 ±0.16° C
AMR-69: −0.4 ± 0.12° C As compared to the saline control, the reduction in fever was highly significant for aminopyrine (t = 6.6, $p < 0.01$) and for AMR-69 (t = 6.3, $p < 0.01$). AMR-69 is an effective anti-pyretic agent.

Protection of Mucous Membranes of the Nasopharynx and Lungs Against Noxious Agents The effectiveness of AMR-69 treatment in affording protection against noxious focal respiratory tract pathology (petechiae, edema, hemmorrhage, focal infection, etc.) was demonstrated upon gross examination of rat lung tissues and microscopic examination of dog lung tissues following treatment of the animals with AMR-69. Special protective effects on the mucous linings of the respiratory system have been confirmed in clinical trials on humans. The tests were carried out on persons exhibiting at least one of the following symptoms: sinusitis, postnasal drip, chronic rhinitis infection, allergic rhinitis, conjunctivitis, headache, earache and sore throat. The pharmaceutical composition was administered orally in capsule form, the capsules being prepared as illustrated in Example 30 and containing approximately 400 mg. of AMR-69 per capsule. In these trials, the noxious effect of acute and chronic infections of the nasopharynx, cranial sinuses were arrested and relieved as evidenced by the cessation of the congestion of the sinuses, disappearance of erythema of the mucous membranes, drainage of the sinuses and the elimination of post-nasal drip. Evidence of relief from the symptom was observed within 30 to 60 minutes after ingestion of the capsule.

Effect On Skin Conditions

The effectiveness of AMR-69 treatment on skin conditions such as dermatitis or itching of the skin, insect (bee) sting, and poison ivy likewise was demonstrated on humans exhibiting these symptoms following the procedure of the proceeding section. Relief from the symptom was rapid in each instance. It was observed in the case of a contact dermatitis condition such as poison ivy that application of AMR-69 in powder form directly to the affected skin areas provided substantially immediate relief from the characteristic itching, and weeping of the affected areas ceased within thirty minutes.

Reduction in Serum Uric Acid Levels (1)

Normal adult albino male and female rats were given repeated graded doses of AMR-69 and the effect upon serum uric acid levels was determined. There were 10 males and 10 females in each group. The control group received the placebo and the drug was administered orally by admixture to the food. The serum uric acid determination was one of a series performed utilizing the Autotechnicon technique (Lofland et al., 1965 Technicon Symposium) using the Standard SMA-12 procedure (based upon procedure of Bittner et al., AM. J. Clin. Path. 40:423, 1963).

The following table clearly demonstrates the reduction in serum uric acid values:

Group I —Placebo - 1.53 ± 0.20 mg.% (Control)
Group II —30 mg./kg. - 1.05 + 0.15 mg.% T = 1.92 (P = 0.06)
Group III —100 mg./kg. - 0.78 + 0.11 mg % T= 3.25 (P<0.01)

The reductions were statistically significant with a T value of 1.92 (P equal to 0.06) at the lower level and at the higher doses the T value was 3.25 (P<0.01).

Microscopic examination of focal tissues of sacrificed animals, at joints of the extremities, in the liver, in muscles and in the kidneys gave no evidence of crystal deposition or uric acid or its salts.

Reduction in Serum Uric Acid Levels (2)

Adult male and female Beagle type dogs from a closed colony weighing approximately 10 to 15 kilograms were utilized in the study. There were seven to nine dogs per group. AMR-69 was given orally in capsules to two groups and the third group received placebo capsules. The reduction in serum uric acid values among AMR-69 treated dogs were significantly different from the control (P<0.05). The method for determining serum uric acid was performed using the Autotechnicon and the SMA-12 series of analyses. The specific method was based upon the procedure of Lofland et al. The mean serum uric acid values obtained with repeated doses of AMR-69 were as follows:

Group I —Placebo - 0.78 ± 0.046 mg.% (Control)
Group II —25 mg/kg - 0.59 ± 0.051 mg.% T = 2.48 (P<0.02)
Group III —75 mg/kg - 0.60 ± 0.049 mg.% T = 2.40 (P<0.05)

Reduction In Serum Glucose Levels

The effect of AMR-69 in lowering glucose level in the serum (blood sugar level) was demonstrated on groups of 10 male and 10 female weanling rats of the Carworth Farms CFE Strain, following in general the procedure outlined under Reduction In Serum Uric Acid Levels (1) above. In a nine week test a group of male rats fed at 600 mg./kg./day of AMR-69 in the diet showed a mean value of 131.8 mg.% of glucose in the serum; a group receiving 900 mg./kg./day of AMR-69 in the diet showed a mean glucose value of 132.6 mg.%; a control male group receiving no AMR-69 showed a mean glucose value of 155.8 mg.%.

A female group fed at a rate of 600 mg./kg./day of AMR-69 in the diet showed a mean glucose value of 144.8 mg.%; a female group fed 900 mg./kg./day of AMR-69 in the diet showed a mean glucose value of 135.8%; a control group receiving no AMR-69 in the diet showed a mean glucose value of 173.0 mg.%.

Acute Toxicity In Mice

In fasted albino mice (Flanders) the $LD_{50}$ for AMR-69 and aminopyrine was determined by standard procedures with the following results:

|  | Oral $LD_{50}$ | Intraperitoneally $LD_{50}$ |
|---|---|---|
| AMR-69 | 580 ± mg./kg. | 420 ± 9 mg./kg. |
| Aminopyrine | 475 ± mg./kg. | 175 ± 9 mg./kg. |

It is apparent that AMR-69 has a significant higher lethal dosage level as compared to aminopyrine and particularly this level is much higher with respect to routes for rapid administration.

Primary Eye Irritation of AMR-69

Six male albino rabbits of the New Zealand strain were incorporated in this study. A dosage of 0.1 ml. of AMR-69-62 (2% Aqueous Solution) was introduced into the conjunctival sac of the left eye of each rabbit; the right eye served as an untreated control.

The six treated rabbit eyes were scored against the corresponding untreated control eyes according to the method of Draize (Draize, J. H. in *Appraisal of the Safety of Chemicals in Foods, Drugs and Cosmetics*, Assoc. of Food and Drug Officials of U.S., Austin, Tex., 1959) at 0.5 minutes, 30 minutes and 3.0 hours after administration of AMR-69.

The group means score at 0.5. minutes was 2.0. The group means scores at 30 munutes and 3.0 hours were 0.0 and 0.0, respectively. According to the Draize evaluation, AMR-69, would not be considered as an irritant to the eye.

Local Toxicity of AMR-69 Intramuscular Injection into Rabbit Leg Muscle

Six healthy adult new Zealand white rabbits from a stock colony were injected into the large muscle mass of the leg with a 2.0 milliliter volume of 2.0% aqueous solution of AMR-69. The response was compared to the intramuscular injection of 2.0 ml. of an isotonic solution of sodium chloride. The animals were carefully observed for any evidence of discomfort for a period of three hours. No discomfort was evident (the animals were not restless; no shuffling of the legs; no licking at the site of injection).

Three hours after the injection, the animals were sacrificed and a careful dissection was made around the injection site of the: (1) skin, (2) subcutaneous fascia, and (3) muscle tissue for a gross examination under a low power binocular mircroscope for any tissue reaction. No evidence of tissue reaction was observed in any of the tissues (skin, subscutaneous fascia or muscle) that could be contributed to the intramuscular injection of AMR-69. Similarly, no tissue reaction was found following the intramuscular injection of the isotonic saline.

One change noted in two rabbits reflected a hemorrhage from a vein which was cut as the hypodermic needle passed into the tissue. After the gross examination, the muscle masses were dissected out, removed and preserved in buffered formalin for histological examination. Stained (hematoxylin) tissue sections made of the excised muscle confirmed the absence of any edema, erythema, chemosis or necrosis. The microscopic examination of the injection sites revealed no difference between those of the isotonic saline and the parenteral AMR-69.

Blood Studies

In series of test animals, including rats, mice, rabbits and dogs, blood studies after administration of AMR-69 for efficacy, and acute and chronic toxicity have shown no indication of blood dyscrasias due to the administration of this agent in therapeutic or sublethal amounts. In lethal amounts, the toxic effects observed were other than those caused by blood dyscrasias and this was borne out by blood and organ studies. This is in contrast to aminopyrine.

Comparison of AMR-69 with Related Pyridones

As already noted in the specification, 5-methyl-1-phenyl-2-(1H)-pyridone (AMR-69) has been observed to possess a striking combination of very effective therapeutic performance together with a low level of toxicity. From the description below, it will be seen that AMR-69 also differs markedly from closely related homologs, such as 5-ethyl-1-phenyl-2-(1H)-pyridone (AMR-94), 3-methyl-1-phenyl-2-(1H)-pyridone (AMR-77) and 1-phenyl-2-(1H)-pyridone (AMR-93) in respect to therapeutic performance as well as in toxicity characteristics.

As to analgesic activity, as already noted under the section entitled "Analgesic Activity", the oral $ED_{50}$ (median analgesic dose) for AMR-69 in rats was 145 ± 26 mg/kg. The oral median "analgesic dose" ($ED_{50}$) for AMR-94 was 160 ± 32 mg./kg. At this dosage, however, all the animals showed marked sedation, Central Nervous System depression, loss of respiratory efficiency, ataxia, and uncoordinated gait. At a low enough dosage of AMR-94 to obviate Central Nervous System depression the "analgesic effect" could not be demonstrated. With AMR-93, the median effective dose was 325 ± 45 mg./kg. At this dosage AMR-93 produced acute bleeding from the nose and an autopsy revealed multiple hemorrhages and edema of the lungs. The oral median effective dose of AMR-77 in rats was 515 ± 45 m.g/kg., approximately one-third to one-fourth the activity of AMR-69 by the oral route.

With respect to anti-inflammatory activity, as already set forth, the oral median effective dose ($ED_{50}$) in rats for AMR-69 was 200 ± 46 mg./kg.; for AMR-94 it was 225 ± 52 mg./kg., accompanied by undesired side-effects as noted above for this compound. No anti-inflammatory effect was observed with AMR-93 and AMR-77 at an oral dosage of 600 mg./kg.

The effective anti-pyretic activity of AMR-69 in rabbits has been noted previously. Administering of AMR-94 caused slight reduction in induced fever which was not considered statistically significant but convulsions were observed in two of the four test animals and marked lowering of normal body temperature was noted even when the animals did not have experimentally induced fever. No significant anti-pyretic activity was observed for AMR-93 or AMR-77.

The lowering in serum uric acid levels shown by AMR-69 in tests on rats and on dogs has been noted. In similar tests on albino male and female rats, AMR-93 and AMR-94 did not show a significant change in serum uric acid level.

Moreover, in tests to demonstrate protection of mucous membranes of the nasopharynx and lungs against noxious agents AMR-69 was found to be effective, as previously noted, whereas AMR-93 and AMR-94 did not show a protective effect and undesirable side effects were evident. Acute deleterious effects on the respiratory system were observed with AMR-77 and there was also no evidence of protective action.

EXAMPLE 1

5-Methyl-1-phenyl-2(1H) pyridone

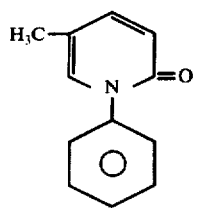

A finely pulverized mixture containing 21.8g of 5-methyl-2-(1H)-pyridone (J. V. Scudi, et al., U.S. Pat. No. 2,947,755), 30,4g of anhydrous potassium carbonate, 0.25g of zinc precipitated copper powder and 40 ml. of iodobenzene is stirred mechanically and refluxed for 18 hours. The mixture is cooled and treated with 150 ml. of benzene, filtered and the filtrate is decolorized with charcoal. The decolorized benzene filtrate is then evaporated to an oil which on trituration with petroleum ether and cooling gives 31.9g (85%) of the product as a brown solid, m.p. 90°-104°. It is crystallized from hot water to yield a white solid melting at 102°-104°.

EXAMPLE 2

5-Methyl-1-(3-nitrophenyl-2)-(1H)-pyridone

The reaction of 24.9 g of 1iodo-3-nitrobenzene (Aldrich Chemical Co.) with 10.9 of 5-methyl-2-(1H)-pyridone by the procedure described in Example 1 affords 16.2g (75%) of 5-methyl-1-(3-nitrophenyl) pyridone.

EXAMPLE 3

5-Methyl-1-(4'-methoxyphenyl)-2-(1H-pyridone

When p-methoxyiodobenzene is substituted for iodobenzene in the procedure of Example 1, 5-methyl-1-(4'-methoxyphenyl)-2-(1H)-pyridone as a crystalline white product is obtained in 78% yield

EXAMPLE 4

5-Methyl-1-p-tolyl-2-(1H)-pyridone

The reaction of p-iodotoluene with 5-methyl-2-(1H)-pyridone by the procedure of Example 1, affords 5-Methyl-1-p-tolyl-2-(1H)-pyridone in 89% yield.

EXAMPLE 5

5-Methyl-1-(3'-trifluoromethylphenyl)-2-(1H)-pyridone

The reaction of 5-methyl-2-(1H)-pyridone with -3-trifluoromethyl-iodobenzene by the procedure of Example 1, gives a 78% yield of 5-methyl-1(3'-trifluoromethylphenyl)-2-(1H)-pyridone.

EXAMPLE 6

1-(4'-Chlorophenyl)-5-methyl-2(1H)-pyridone

The reaction of 5-methyl-2-(1H)-pyridone and 1-chloro-4-iodobenzene (Aldrich Chemical Company) in the procedure of Example 1 yields 1-(4'-chlorophenyl)-5-methyl-2-(1H)-pyridone as a white crystalline solid in 75% yield.

EXAMPLE 7

5-Methyl-1-(2'-naphthyl)-2-(1H)-pyridone

Following substantially the procedure of Example 1, B-iodonaphthalene is reacted with 5-methyl-2-(1H)-pyridone to give 5-methyl-1-(2'-naphthyl)-2-(1H)-pyridone in 74% yield.

EXAMPLE 8

5-Methyl-1-(1-naphthyl)-2-(1H)-pyridone

5-Methyl-1-(1-naphthyl)-2-(1H)-pyridone is prepared by the reaction of 5-methyl-2-(1H)-pyridone and α-iosonaphthalene following the procedure of Example 1 but substituting anhydrous sodium carbonate for the potassium carbonate; yield 68%.

EXAMPLE 9

3-Methyl-1-phenyl-2-(1H-pyridone

A mixture of 10.9 g. of 3-methyl-2-(1H)-pyridone and 20 ml. of iodobenzene when caused to react under the conditons as described in Example 1, yields 17.2g. (93%) of 3-methyl-1-phenyl-2-(1H)-pyridone.

EXAMPLE 10

6-Methyl-1-phenyl-2-(1H)-pyridone

The condensation of 10.9g. of 6-methyl-2-(1H)-pyridone (Adams, and Schrecker, J.A.C.S.71 (1949)) with 20 ml. of iodobenzene under the reaction conditions as in Example 1 affords 18.7g. (79% ) of 6-methyl-1-phenyl-2-(1H)-pyridone [M. Shamma and P. D. Rosenstock, J. Org. Chem. 26, 2586 (1961)].

EXAMPLE 11

3,6-Dimethyl-1-phenyl-2-(1H)-pyridone

As described in Example 1, 12.3g. of 2.6-dimethyl-2-(1H)-pyridone is reacted with 20 ml of iodobenzene to yield 16.1g. (81%) of 3,6-dimethyl-1-phenyl-2-(1H)-pyridone.

EXAMPLE 12

Methyl-1(2'thienyl)-2-(1H)-pyridone

Following the method essentially of Example 1, 2-bromothiophene is reacted with 5-methyl-2-(1H)-pyridone to give 5-methyl-1(2' thienyl)-2(1H)-pyridone; yield 82%.

EXAMPLE 13

1-(2'-Furyl)-5-methyl-2-(1H)-pyridone

In the manner described in Example 1, 2-bromofuran and 5-methyl-2(1H)-pyridone are reacted to provide 1-(2'-furyl)-5-methyl-2-(1H)-pyridone; yield 63%

EXAMPLE 14

5-Methyl-1-(5'-quinolyl)-2-(1H)-pyridone

5-Iodoquinoline reacts with 5-methyl-2-(1H)-pyridone as described in Example 1, and affords 5-methyl-1-(5'-quinolyl)-2 (1H)-pyridone in 85% yield.

EXAMPLE 15

5-Methyl-1-(4'-pyridyl)-2-(1H)-pyridone

5-Methyl-1-(4'-pyridyl)-2-(1H)-pyridone is obtained in 74% yield when 4-bromopyridone is substituted for iodobenzene in Example 1.

EXAMPLE 16

5-Methyl-1-(3' pyridyl)-2-(1H)-pyridone

3-Bromopyridine is substituted for iodobenzene in the procedure of Example 1 to give 5-methyl-1-(3'-pyridyl)-2-(1H)-pyridone in 71% yield.

EXAMPLE 17

5-Methyl-1-(2'-pyridyl)-2-(1H)-pyridone

Following the general procedure outlined in Example 1, 2-bromopyridine is caused to react with 5-methyl-2-(1H)-pyridone to yield 83% of 5-methyl-1(2'pyridyl)-2-(1H)-pyridone.

EXAMPLE 18

5-Methyl-1-(2'quinolyl)-2-(1H)-pyridone

The preparation of 5-methyl-1-(2'-quinolyl)-2-(1H)-pyridone is carried out as in Example 1 using 5-methyl-2(1H)-pyridone and 2-bromoquinoline; yield 71%.

EXAMPLE 19

5-Methyl-1-(4'-quinolyl)-2-(1H)-pyridone

5-Methyl-2-(1H)-pyridone is condensed with 4-bromoquinoline as described in Example 1 to afford 5-Methyl-1-(4'-quinolyl)-2-(1H)-pyridone in 65% yield.

EXAMPLE 20

5Methyl-1-(2' thiazolyl)-2-(1H)-pyridone

5-Methyl-1-(2'thiazolyl)-2-(1H)-pyridone is obtained by the reaction of 2-chlorothiazole with 5-methyl-2(1H)-pyridone following the general method of Example 1; yield 69%.

EXAMPLE 21

1-(2'Imidazolyl)-5-methyl-2-(1H)-pyridone

Following essentially the general procedure outlined in Example 1, the reaction of 5-methyl-2-(1H)-pyridone with 2-chloroimidazole affords 1-(2'-imidazolyl)-5-methyl-2-(1H)-pyridone in 82% yield.

EXAMPLE 22

5-Ethyl-1-phenyl-2-(1H)-pyridone

Iodobenzene when caused to react with 5-ethyl-2-(1H)-pyridone following the general procedure outlined in Example 1, an 84% yield of 5-ethyl-1-phenyl-2-(1H)-pyridone is obtained.

EXAMPLE 23

1-Phenyl-2-(1H)-pyridone

Following substantially the procedure of Example 1, 2-(1H)-pyridone is condensed with iodobenzene to give the 1-phenyl-2-(1H)-pyridone in 82% yield as a crystalline white product.

EXAMPLE 24

1-(4'-Nitrophenyl)-2-(1H)-pyridone

The reaction of 24.9g. of 1-iodo-4-nitro-benzene (Aldrich Chemical Co.) with 9.5g. of 2-(1H)-pyridone in presence of 0.1g. of copper powder by the procedure described in Example 1 affords 17.3g. (80%) of 1-(4-nitrophenyl)-2-(2H)-pyridone.

EXAMPLE 25

1,3-Diphenyl-2-(1H)-pyridone 1,3-Diphenyl-2(1H)-pyridone is obtained in 80% yield by causing 3-phenyl-2(1H)-pyridone (Brit. Pat. No. 1,238,959; B. E. Witzel) to react with iodobenzene as described in Example 1.

EXAMPLE 26

1-Phenyl-3-(4'-chlorophenyl)-2-(1H)-pyridone

1-Phenyl-3-(4'-chlorophenyl)-2-(1H)-pyridone is realized in 78% yield by the reaction of 3-(p-chlorophenyl)-2-(1H)-pyridone (Bruce E. Witzel, Brit, Pat. No. 1,238,959) with iodobenzene as described in Example 1.

EXAMPLE 27

1,3-Diphenyl-5-methyl-2-(1H)-pyridone

5-Methyl-3-phenyl-2-(1H)-pyridone (B. E. Witzel, et al. Brit. Pat. 1,238,959) is reacted with iodobenzene as in Example 1 to give 1,3-Diphenyl-5-methyl-2-(1H)-pyridone in 77% yield.

EXAMPLE 28

3-(4'Chlorophenyl)-5-Methyl-1-phenyl-2-(1H)-pyridone 3-(4'Chlorophenyl)-5-methyl-1-phenyl-2-(1H)-pyridone is prepared in 82% yield by the reaction of 3-(p-chlorophenyl)-5-methyl-2-(1H)-pyridone (B. E. Witzel et al. Brit. Pat. No. 1,238,959) with iodobenzene as described in Example 1.

EXAMPLE 29

5-Methyl-3-phenyl-1-(2'thienyl)-2-(1H)-pyridone

The reaction of 2-thienyl bromide with 5-methyl-3-phenyl-2-(1H)-pyridone by the procedure outlined in Example 1 but substituting anhydrous lithium carbonate for the potassium carbonate provides 5-methyl-3-phenyl-1-(2'thienyl)-2(1H)-pyridone in 67% yield.

EXAMPLE 30

Therapeutic dosage forms of 5-methyl-1-phenyl-2-(1H)-pyridone

The excipients indicated below are the excipients commonly used for making Pharmaceutical tablets. Such tablets preferably have a concentration of the active constituent in the range generally between 100–500 mg. per tablet.

| | |
|---|---|
| AMR-69 (5-methyl-1-phenyl-2(1H)-pyridone) | 100–500 mg. |
| Polyvinylpyrrolidone | 2–4 mg. |
| Silicic acid | 1 mg. |
| Corn starch | 40–80 mg. |
| Magnesium stearate | 1–5 mg. |
| Talc | — |
| Milk sugar | Q.s. |

The above mixture with commonly used moistening agents such as glucose syrups and water is granulated and then pressed in a tablet making machine.

It will be understood that formulation with the active compound can be prepared in the form of pills, dragees, capsules, cachets, suppositories, sustained release pulvules and similar pharmaceutical forms.

The posology of the compound in dosage form of course should be determined by a physician. The individual dose should be adapted and adjusted to the patient's reactivity, the severity of the symptoms, the age and weight and the general physical condition of the patient. For tests to be carried out on human subjects a recommended dosage would be from about 200 mg. to about 400 mg. for an average subject having a weight of about 75 kilograms. A preferred range would be from 300 mg. to 400 mg. Because of the low toxicity shown by AMR-69, higher dosages could be used if the need were indicated. If desired or necessary, the dosage noted above can be repeated within 4 to 6 hours.

EXAMPLE 31

Therapeutic Solution Intended for Injection

| | |
|---|---|
| 5-methyl-1-phenyl-2(1H)-pyridone | 100 mg. |
| Sodium chloride | 2.5 mg. |
| Buffers, distilled water[1]   Q.s. Ad | 10 mg. |

[1] 10 mg. AMR-69/cc

The above formulation may then be packaged into multiple dose vials or into individual ampules.

Similarly, suspensions and solutions in liquid media such as oils, syrups, tinctures and solvent solutions may be prepared. Pertrolatum may be used as a vehicle for topical application.

The foregoing examples are presented to indicate the nature and utility of this invention. The specific examples constitute preferred embodiments of the practice of this invention and the results indicated set forth the true nature and utility of this invention. It is understood that these examples are presented as illustrative and they are not intended to limit in any way the scope of this invention. All art-recognized equivalents of the specific embodiments and ingredients set forth are intended.

I claim:

1. A method for reducing the uric acid level in the serum of a mammal in need of such reduction which comprises administering to said mammal a therapeutically effective amount of 5-methyl-1-phenyl-2-(1H)-pyridone.

2. The method of claim 1 wherein the mammal is a human.

3. The method of claim 2 wherein the 5-methyl-1-phenyl-2-(1H)-pyridone is administered in dosage unit form.

4. The method of claim 3 wherein the dosage unit contains between 100 and 500 mg. of 5-methyl-1-phenyl-2-(1H)-pyridone.

5. The method of claim 3 wherein the dosage unit contains between 300 and 400 mg. of 5-methyl-1-phenyl-2-(1H)-pyridone.

6. The method of claim 3 wherein the dosage unit is administered every 4 to 6 hours.

* * * * *